United States Patent
Furumoto et al.

[19]

[11] Patent Number: 6,045,548
[45] Date of Patent: *Apr. 4, 2000

[54] ALEXANDRITE LASER SYSTEM FOR HAIR REMOVAL AND METHOD THEREFOR

[75] Inventors: Horace W. Furumoto, Wellesley; George Cho, Hopkinton, both of Mass.; Eric Koschmann, Hudson; Antonio G. Rizzo, Nashua, both of N.H.

[73] Assignee: Cynosure, Inc., Chelmsford, Mass.

[ * ] Notice: This patent is subject to a terminal disclaimer.

[21] Appl. No.: 09/158,056

[22] Filed: Sep. 22, 1998

Related U.S. Application Data

[63] Continuation of application No. 08/744,344, Nov. 7, 1996, Pat. No. 5,871,479.

[51] Int. Cl.$^7$ .................................................. A61N 5/06
[52] U.S. Cl. ........................................................... 606/9
[58] Field of Search ............................... 606/2, 3, 9, 10, 606/12, 14, 15, 16, 17

[56] References Cited

U.S. PATENT DOCUMENTS

| | | | |
|---|---|---|---|
| 3,538,919 | 11/1970 | Meyer ..................... | 128/398 |
| 3,693,623 | 9/1972 | Harte et al. . | |
| 3,769,963 | 11/1973 | Goldman et al. ........ | 128/2 R |
| 3,794,028 | 2/1974 | Mueller et al. .......... | 128/216 |
| 3,834,391 | 9/1974 | Block . | |
| 3,900,034 | 8/1975 | Katz et al. ............... | 128/395 |
| 4,336,809 | 6/1982 | Clark ....................... | 128/665 |
| 4,388,924 | 6/1983 | Weissman et al. . | |
| 4,461,294 | 7/1984 | Baron . | |

(List continued on next page.)

FOREIGN PATENT DOCUMENTS

| | | | |
|---|---|---|---|
| 0 142 671 A1 | 5/1985 | European Pat. Off. | ......... A61B 17/36 |
| 0 458 576 A2 | 11/1991 | European Pat. Off. | ......... H01S 3/08 |
| 0 575 274 A1 | 12/1993 | European Pat. Off. | ......... A61C 1/00 |
| 91/12050 | 8/1991 | WIPO | ............... A61N 5/06 |
| WO 91/18646 | 12/1991 | WIPO | ............... A61N 5/06 |
| WO 95/15725 | 6/1995 | WIPO | ............. A61B 17/41 |
| 95/335518 | 12/1995 | WIPO | ............... A61N 5/06 |
| 96/23447 | 8/1996 | WIPO | ............. A61B 17/36 |

OTHER PUBLICATIONS

Finkelstein, L.H., "Epilation of Hair–Bearing Urethral Grafts Utilizing the Neodymium: YAG Surgical Laser," *Lasers in Surgery and Medicine* 10:182–193 (1990).

Goldman, M.P., "Sclerotherapy—Treatment of Varicose and Telangiectatic Leg Veins," *Second Edition, Mosby*, pp. 454–467 (No Date Given).

"Temperature Indicating Tab, Crayons, Lacquers, and Pellets," pp. F5–F6, F13, F19 (Advertisement Brochure—No Date Given).

"Hydrogel Dressings Contain Particles During Laser Therapy," *Dermatology Times* 94–01, ISSN–01966197, p. 26 (1994).

Dover, J.S., et al., "Pigmented Guinea Pig Skin Irradiated with Q–Switched Ruby Laser Pulses," pp. 43–49, *Arch Dermatol*, vol. 125 (Jan. 1989).

Primary Examiner—Lee Cohen
Assistant Examiner—Sonya Harris-Ogugua
Attorney, Agent, or Firm—Hamilton, Brook, Smith & Reynolds, P.C.

[57] ABSTRACT

A long pulse alexandrite laser hair removal system is disclosed using light pulses of greater than 1 msec and fluences between 10 and 50 J/cm$^2$. The use of an alexandrite laser allows good penetration while still achieving an acceptable combination of hemoglobin and melanin absorption. The use an index-matching application on the skin sections to be treated is also described. This substance will be absorbed into the epidermal layer to provide better coupling of the laser light into the skin. Also, and most advantageously, it will reduce reflections at the epidermal-dermal junction, which can lead to the damage of the skin. Also a topical thermal or photochromic indicator is suggested since skin irradiation in the near-infrared generally does not produce any characteristic skin color change as is found when using pulsed dye lasers, for example.

5 Claims, 5 Drawing Sheets

U.S. PATENT DOCUMENTS

| | | |
|---|---|---|
| 4,601,037 | 7/1986 | McDonald .................................. 606/10 |
| 4,608,978 | 9/1986 | Rohr . |
| 4,617,926 | 10/1986 | Sutton . |
| 4,813,412 | 3/1989 | Yamazaki et al. . |
| 4,829,262 | 5/1989 | Furumoto .................................. 330/4.3 |
| 4,862,888 | 9/1989 | Yessik ..................................... 606/4 X |
| 5,059,192 | 10/1991 | Zaias ........................................ 606/9 |
| 5,071,416 | 12/1991 | Heller et al. ............................. 606/3 |
| 5,217,455 | 6/1993 | Tan ........................................... 606/9 |
| 5,226,907 | 7/1993 | Tankovich ............................. 606/9 X |
| 5,255,277 | 10/1993 | Carvalho ................................. 372/38 |
| 5,269,777 | 12/1993 | Doiron et al. ............................ 606/7 |
| 5,282,797 | 2/1994 | Chess ....................................... 606/9 |
| 5,290,273 | 3/1994 | Tan ........................................... 606/9 |
| 5,344,418 | 9/1994 | Ghaffari ................................... 606/9 |
| 5,405,368 | 4/1995 | Eckhouse ................................. 607/88 |
| 5,423,800 | 6/1995 | Ren et al. ................................. 606/4 |
| 5,425,728 | 6/1995 | Tankovich ................................ 606/9 |
| 5,486,172 | 1/1996 | Chess ....................................... 606/20 |
| 5,498,935 | 3/1996 | McMahan et al. .................... 606/12 X |
| 5,527,350 | 6/1996 | Grove et al. ............................. 607/89 |
| 5,558,667 | 9/1996 | Yarborough et al. ...................... 606/9 |
| 5,595,568 | 1/1997 | Anderson et al. ......................... 606/9 |
| 5,620,478 | 4/1997 | Eckhouse ................................. 607/88 |
| 5,624,435 | 4/1997 | Furumoto et al. ......................... 606/9 |
| 5,630,811 | 5/1997 | Miller ....................................... 606/9 |
| 5,632,741 | 5/1997 | Zavislan et al. .......................... 606/9 |
| 5,647,866 | 7/1997 | Zaias et al. ............................... 606/9 |
| 5,735,844 | 4/1998 | Anderson et al. ......................... 606/9 |
| 5,868,732 | 2/1999 | Waldman et al. ......................... 606/9 |
| 5,879,346 | 3/1999 | Waldman et al. ......................... 606/9 |

ALEXANDRITE LASER SYSTEM FOR HAIR REMOVAL AND METHOD THEREFOR

RELATED APPLICATIONS

This application is a Continuation of U.S. patent application Ser. No. 08/744,344, filed Nov. 7, 1996, now U.S. Pat. No. 5,871,479, which is related to U.S. Ser. No. 08/745,133, filed Nov. 7, 1996, the teachings of which are incorporated herein by this reference in their entirety.

BACKGROUND OF THE INVENTION

Historically, there have been a number of options for the permanent removal of hair. Electrolysis has been the most commonly selected approach, in which an operator, usually a electrologist, attaches an electrode to each individual hair shaft, with the patient typically holding a second electrode. An electrical current is then passed through the hair shaft and the hair follicle through the papilla. This precisely directed current can induce permanent injury in the follicle and papilla, stopping the future production of the hair shaft.

Problems exist with the electrolysis technique, however. The success with which hair is permanently removed varies greatly from patient to patient. Moreover, the process is slow since each hair follicle must be individually treated, and there is some discomfort associated with the electric current.

The removal of hair using lasers is another approach that has found only limited success. Numerous techniques have been taught in the prior art. Each, however, suffers from drawbacks such as poor ultimate success in stopping hair growth even after multiple treatments, excessive injury to the tissue surrounding the hair follicles and papilla, and excessively large and expensive laser systems.

One approach relies on a pulsed laser source and the use of an exogenous absorber. A commercially available hair dye solution is first applied to the skin containing the unwanted hair and allowed to migrate along the hair shafts and into the follicles. The skin is then irradiated with a spot size of approximately 0.5 centimeters using a Q-switched YAG laser, or other short pulsed laser system. The pulse durations used by the lasers tend to be short, 15 nsec for the Q-switched laser. It appears that the sub-microsecond pulse durations shocks the hair follicle, which stops hair production, but only for a limited time. After months, the follicle again begins to produce hair, requiring further treatments or other techniques to yield any lasting success.

Other approaches have been proposed that rely on flashlamps, instead of lasers. This has the advantage of a less expensive, reasonably portable light source, but flashlamps create their own control problems. It is difficult to deliver light from the flashlamp to the skin, so that it must be placed in proximity to the skin. The reflectors that surround the flashlamp and collect the light and direct it to the skin must be precisely built and calibrated. Any error can cause hot spots in the spatial energy distribution. This can lead to under-treatment in some areas and burning in others. Moreover, the bandwidth of the light from these flashlamps is broad, usually including the visible and stretching into the longer infrared wavelengths. These longer wavelengths are well absorbed by water that occupies the skin. Thus, the light from these sources tends to penetrate very poorly, which leads to higher fluence levels to sufficiently treat deeper-lying hair producing structures with the concomitant risk of burning or damaging the skin.

Still other approaches use laser light delivery systems that inject light into only a single hair follicle at a time. These have the advantage of a reduced concern for damaging tissue between hair follicles but have many of the same disadvantages associated with the electrolysis. That is, each individual hair and hair follicle must be separately treated.

Long pulse ruby lasers have recently been used in hair removal. The high energy ruby lasers, however, are generally large, inefficient types of laser light generators, when very long pulses are generated.

SUMMARY OF THE INVENTION

The present invention is directed to a long pulse alexandrite laser hair removal system. The use of an alexandrite in the present invention allows operation in the near-infrared, specifically in a 100 nm range surrounding 760 nm, and ideally at approximately 755 nm and a surrounding 50 nm range. Infrared in this range allows good penetration while still achieving an acceptable ratio of hemoglobin to melanin absorption. Moreover, the use of a long pulse alexandrite laser, in contrast to short-pulse Q-switched laser typically used on pigmented lesions and tattoos, yields two advantages: 1) the pulse duration now can match the thermal relaxation times of the targeted hair structures within the skin; and 2) the removal of the Q-switching element makes a laser system that is less temperamental and easier to operate.

In specific embodiments, it is desirable to use an index-matching application on the skin sections to be treated. This substance covers the epidermal layer to provide better coupling of the laser light into the skin.

In other aspects of the embodiments, a topical indicator is also preferably used on the skin. Skin irradiation in the near-infrared generally does not produce any characteristic skin color change as is found when using dye pulsed lasers, for example. Thus, it is difficult to know exactly what portions of the skin have already been irradiated during a treatment session. The visual indicator is thermo- or photo-responsive or otherwise responsive to the laser light pulse to generate a visible change. This provides the operator with a record of those parts of the skin that have already been treated.

The skin is preferably treated with laser pulses of greater than a millisecond, preferably approximately 5 to 50 msec. Each pulse should contain a fluence of between 10 and 50 Joules per square centimeter ($J/cm^2$). During each treatment session, each treated section of the skin is preferably irradiated with one such pulse, although multiple pulses could be used. Even so, permanent and complete laser removal may require three to four repeat treatment sessions, with weeks to months long dwell times between each session.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

DETAILED DESCRIPTION OF THE PREFERRED EMBODIMENT

Figure 1:
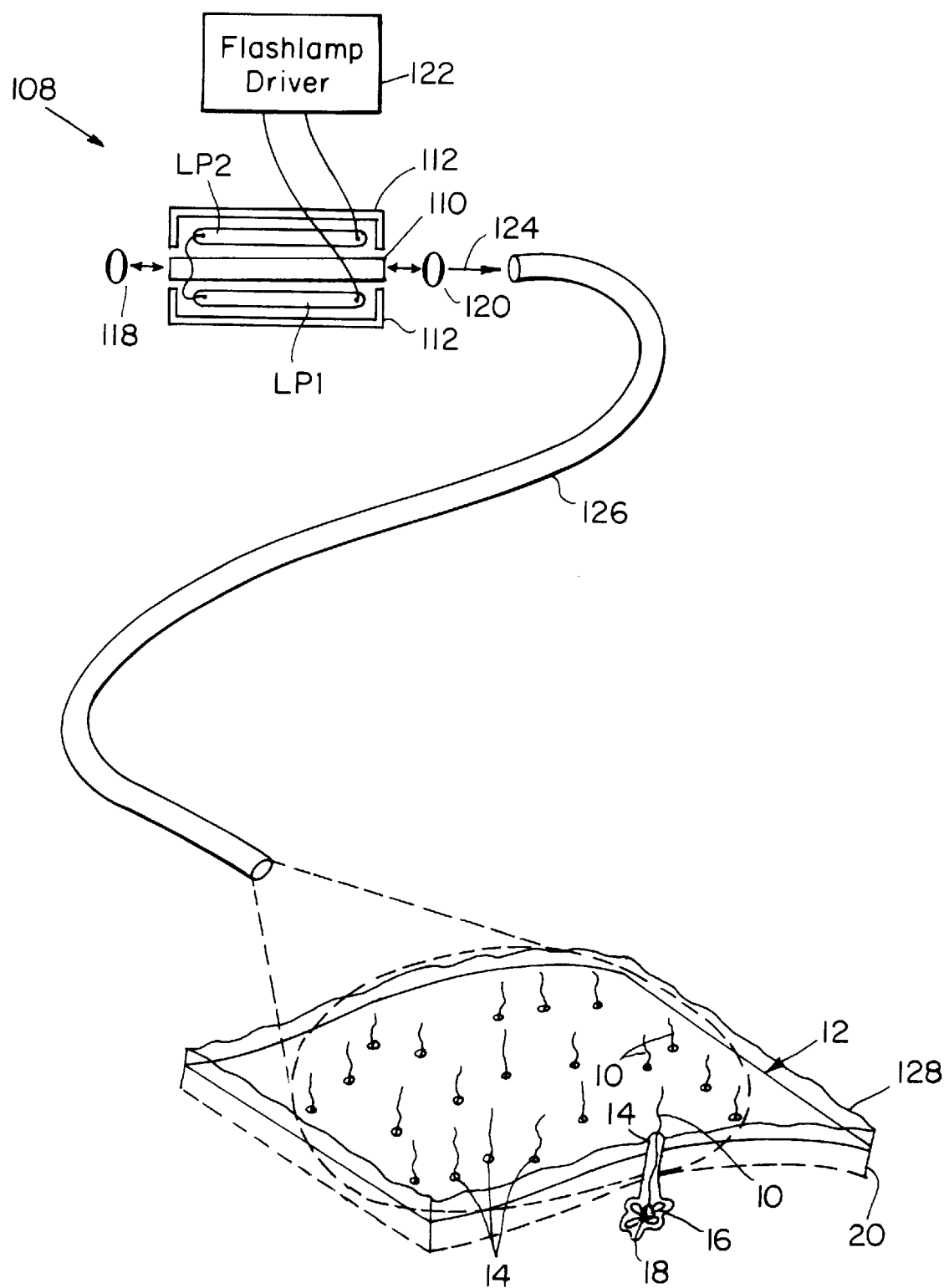
FIG. 1 is a schematic view of the inventive alexandrite laser system illustrating its use for the treatment of hair-bearing skin.

FIG. 1 shows an alexandrite laser system for hair removal, which has been constructed according to the principles of the present invention. An alexandrite laser 108 generally comprises one or more flashlamps LP1 and LP2 that are disposed around a usually centrally located alexandrite crystal gain medium 110. The flashlamps 114 directly irradiate the gain medium or via the associated reflector 112. The flashlamps LP1,LP2 are driven by a flashlamp driver 122.

The alexandrite crystal 110 generates a laser light output pulse 124 in the laser's resonant cavity, which is defined by mirrors 118 and 120. Mirror 120 is only partially reflecting and thus provides the laser's output aperture. The reflectance of the output aperture mirror 120, however, is relatively high. Generally, in Q-switched lasers, the reflectance of the output aperture mirror will be less than or equal to 50%. This is due to the fact that high peak pulse powers are to be generated, but only for a short pulse duration. In contrast, in the present long pulse alexandrite laser system, the driving factor is to increase the laser's efficiency when operating just above the laser's pumping threshold. As a result, the reflectance of mirror 120 in the present invention is preferably greater than or equal to 80%.

Another design factor is the length of the resonant cavity as defined by mirrors 118 and 120. In the preferred embodiment, the cavity is relatively short, 15 inches or approximately 45 centimeters. The mirrors 118 and 120 have large radii of curvature forming a near concentric resonant cavity. This configuration further decreases losses and increases efficiency, but beam divergence also increases.

The pulse from the cavity is preferably coupled into a medical delivery system 126, which can take any one of a number of different forms including fiber optics. In the illustrated example, it is a fiber optic light guide that transmits the pulse from the laser to the hair-bearing skin 12 that is to be treated. Specifically, a quartz fiber delivery system can be used. The longer pulses that are characteristic of the present invention allows the use of the quartz. Although relatively high energies are generated with the laser light output pulse 124, 20–40 J, the low peak powers avoid damage to the delivery system. In either case, the core diameter should be between 1 and 1.5 millimeters. This relatively large diameter accepts the high beam divergence created by the resonant cavity using lens with easily available focal lengths from 2 to 10 cm.

Figure 2B:
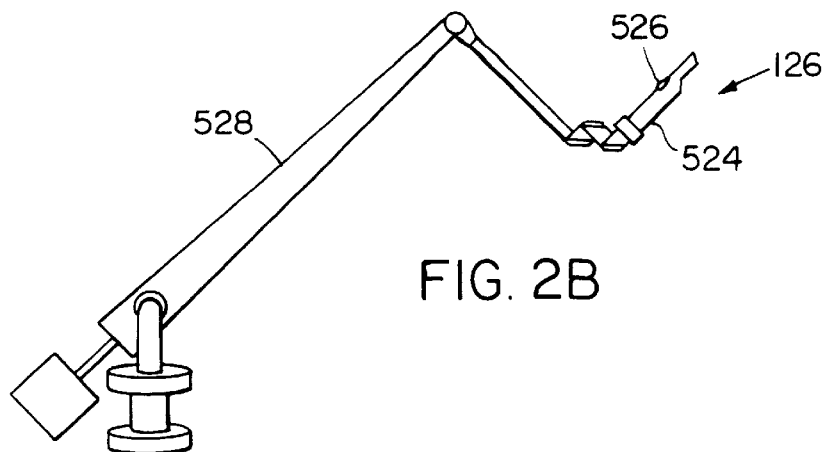
FIGS. 2A and 2B are schematic views of two embodiments of the alexandrite laser system.
Figure 2A:
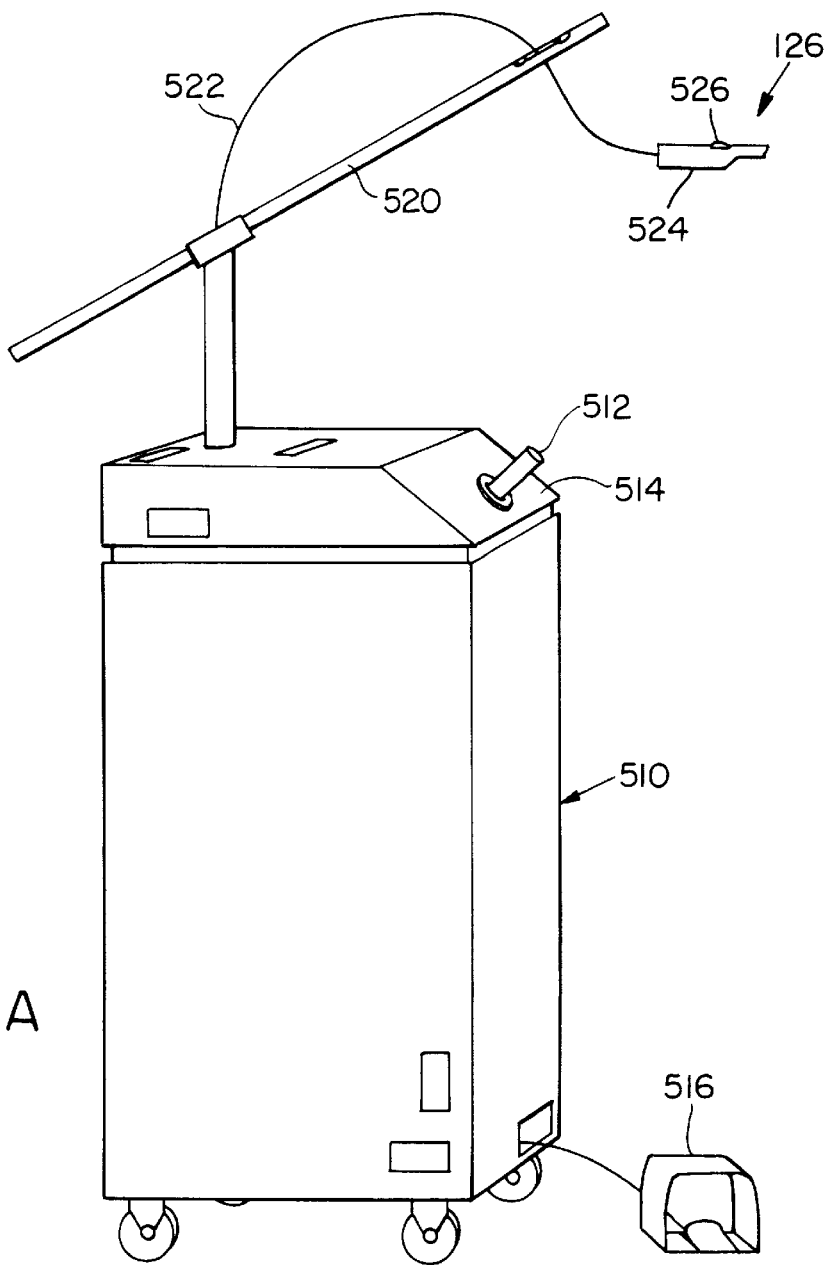

FIGS. 2A and 2B show two implementations of the laser system that would be appropriate for in-office treatment. It comprises a main unit 510 that has a calibration port 512 and a front control panel 514. A foot switch is provided for convenient control. A swing arm 120 holds the optical delivery fiber 522 that ends in a handpiece 524. The handpiece has a finger switch 526 also for activation. FIG. 2B shows another embodiment using an articulated arm 528 as in the delivery system 126. This embodiment is compatible with the quartz fiber delivery system.

A similar system is disclosed in related U.S. patent application Ser. No. 08/745,133, filed Nov. 7, 1996, entitled "Method For Treatment of Unwanted Veins and Device Therefor", by Horace W. Furumoto, et al., the teachings of which are incorporated herein by this reference in their entirety.

The use of the alexandrite laser is preferred to other laser systems for a number of reasons. Alexandrite is tunable through a 100 nm range surrounding 760 nm. This range has a number of advantages relative to ruby or pulsed dye lasers that have been used in the past.

Figure 3:
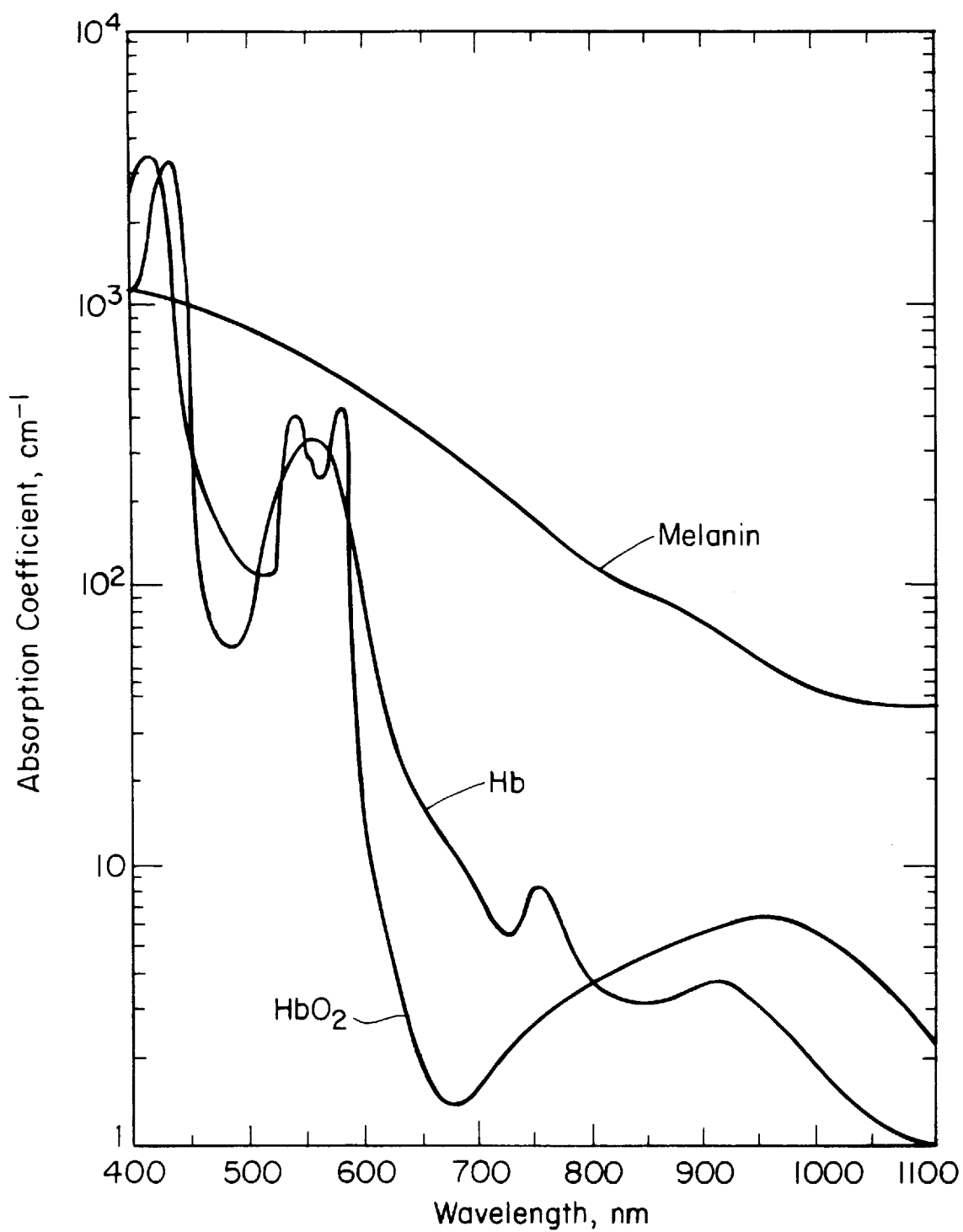
FIG. 3 is a plot of the spectral absorption of hemoglobin and melanin.

Pulsed dye lasers operating in the 577–585 nm range are well absorbed by the deoxy-hemoglobin (Hb) and oxy-hemoglobin ($HbO_2$) relative to the melanin, as shown in FIG. 3. This provides good selectivity. The problem, however, is that the total absorption of the melanin is very high. As a result, the laser light does not penetrate very deeply into the dermal layer. To effectively render inactive the hair-producing skin structures, the light must penetrate deeply, up to 5 millimeters, to the hair papilla and the nutrient blood vessels that surround it.

Ruby lasers operating at 694 nm do achieve good penetration since the absorption of melanin is incrementally lower at this wavelength. The problem here, however, is that the Hb and $HbO_2$ have low absorptions at this wavelength, as also shown in FIG. 3. To effectively and permanently stop the growth of a hair, the light must penetrate down to the papilla and be absorbed in the papilla but also the surrounding nutrient blood vessels. Ruby lasers do not achieve this destruction because of their poor blood absorption. This is why the prior art teaches the use of exogenous absorbers. These absorbers, however, do not solve the problem since they do not reach to the depth of the papilla.

In contrast, in the 50 nm range surrounding 755 nm, where the inventive alexandrite laser system operates, melanin absorption is lower, compared to the ruby laser. Thus, better penetration is achieved down to the hair's papilla to the approximately five millimeter depth. Somewhat more importantly, however, is the fact that the absorption of Hb peaks in this range and the absorption of $HbO_2$ is substantially higher than at the ruby laser's wavelength. These factors combine to allow laser light to 1) penetrate to the depth of the papilla and blood vessels supplying the papilla; and 2) then be absorbed by the melanin, and hemoglobin containing blood cells in those vessels. Because of the long pulse durations, blood in small vessels between the surface of the skin and the papilla diffuse its heat to surrounding tissue and is not heated to denaturation. Blood in the papilla is heated because the heat is confined within the papilla which is a large structure.

The use of the alexandrite laser has further, more utilitarian, advantages. Long pulse dye and ruby lasers tend to be larger, inefficient devices. Moreover, pulsed dye lasers have the added drawback of requiring the dye gain media, which are not efficient in the infrared. In contrast, long pulse alexandrite laser systems are substantially smaller, and the conversion of energy from the flashlamps into the output laser light pulse is much more efficient than either dye or ruby lasers.

A still further advantage relative to dye lasers is the fact that alexandrite lasers generally allow longer pulse durations than dye lasers. This factor is relevant because the pulse duration of the irradiating light is important for selectivity. If the pulse duration is too long, the heat absorbed by the papilla and surrounding vessels would diffuse into the surrounding dermal tissue so that the papilla and blood vessels would not be selectively heated to the degree necessary to destroy only those structures. If the pulse durations are too short, however, the smaller light absorbing chemical species, such as the blood hemoglobin or melanin, and smaller blood vessels will not be cooled by heat diffusion and the epidermis will be overheated and burn. This effect can cause purpura, bleeding, and burning but also generally is not effective at permanently stopping hair growth. This is why the shorter pulse duration ruby lasers only find limited success in permanently removing the hair.

In the preferred embodiment, the laser system 108 irradiates the treated skin section with laser light output pulses having durations of between 1 and 40 msec. The best results, however, have been achieved using pulses of approximately 5 to 10 msec or longer.

Use of the long pulse alexandrite laser 108 also has certain advantages relative to other alexandrite laser systems used in the prior art for tattoo removal and pigmented lesion treatment. Historically, alexandrite lasers generally have been viewed as difficult to implement. The Q-switching element in the laser cavity made operation of the laser unstable. In the present laser system 108, the Q-switching element is removed and the gain medium laser is driven into the longer pulse durations. This improves the operation of the laser.

The invention additionally, preferably includes the use one or more topical applications on the skin to be treated. Mineral oil, K-Y® jelly or any other wet, penetrating, biocompatable application is preferably applied in a layer 128 over the hair-bearing skin 12 that is to be then laser treated. The layer provides gross refractive index-matching.

In addition to the index-matching layer, a thermo- or photo-sensitive irradiation marker is included as a separate layer to the index-matching layer or in a common vehicle with the index-matching substance. This thermochromic or photochromic marker preferably changes color or state in response to being exposed by the laser light output pulse. This indicates to the operator those portions of the skin surface 12 that have been exposed. The marker may be a temperature indicating crayon or liquid that liquifies at a known temperature, such as sold commercially by Omega Engineering, Inc., although bio-compatibility has not yet been confirmed with these products.

The use of a thermochromic or a photochromic marker is useful when irradiating the skin with light in the near-infrared. When skin is exposed to pulsed light in the shorter frequencies, such as 577–585 nm, there is an instantaneous purpuric effect which acts as a record of those portions of the skin that have been treated. This effect does not occur when the skin is irradiated with the near-infrared. Use of the marker which changes color or state, for example, in response to the light or indicated heat, however, provides the helpful indication of those portions of the skin that have been treated.

Figure 4:
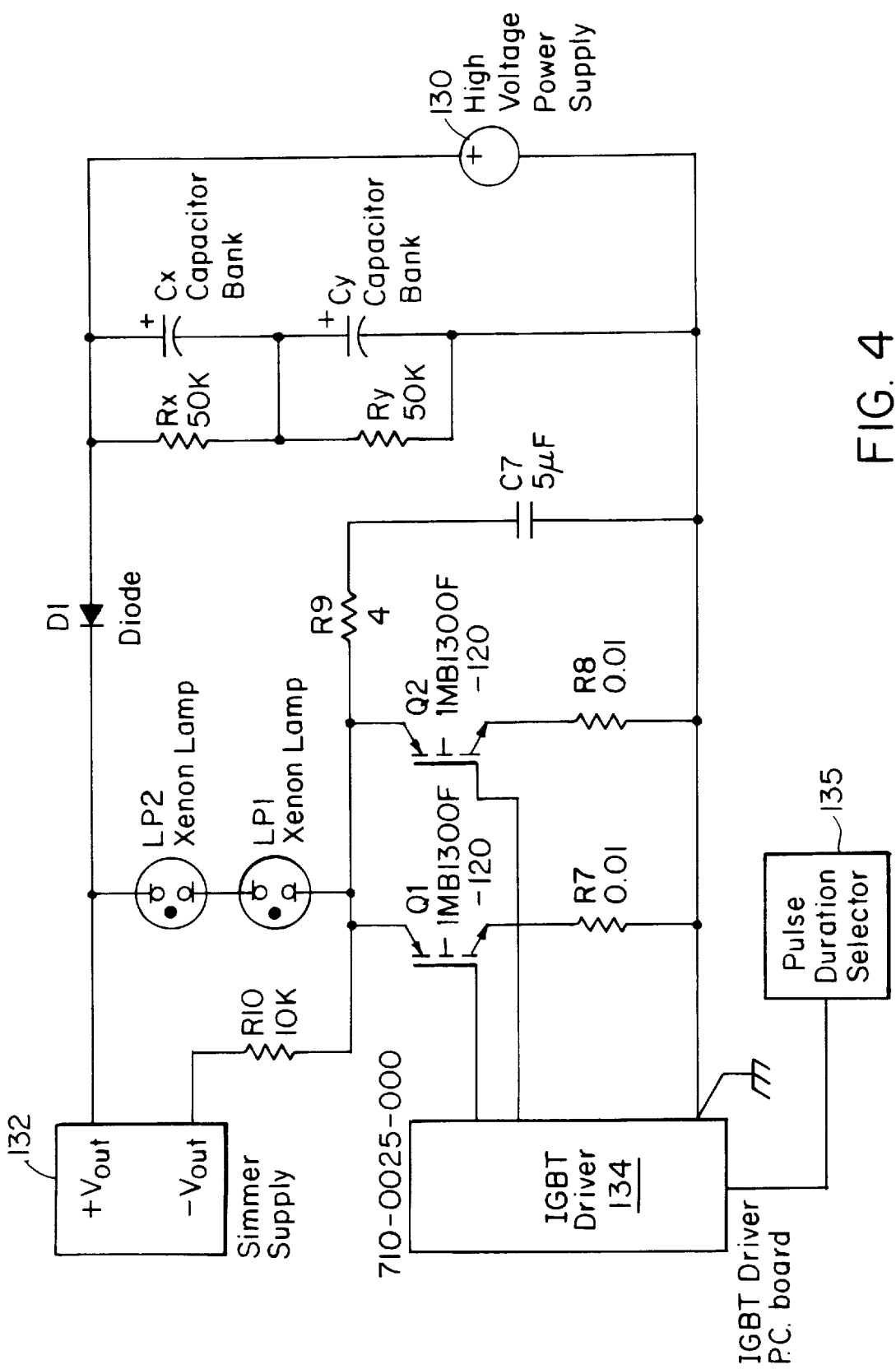
FIG. 4 is a circuit diagram showing an inventive flashlamp driver for the laser system.

FIG. 4 is a circuit diagram showing the flashlamp driver 122. Generally, the circuit has a simmer power supply 132 and a high voltage power supply 130 for two Xenon flashlamps, LP1 and LP2. As is known, the simmer supply 132 maintains the flashlamps LP1, LP2 at an operational temperature, so that when they are driven by the high voltage power supply, the light generation is virtually instantaneous. Two series capacitor banks, Cx, Cy, with parallel resistors Rx and Ry, respectively, are charged by the high voltage power supply to supplement the power provided to the flashlamps LP1, LP2 when pumping the alexandrite.

Conventionally, laser flashlamps are driven by the high voltage power supply through a passive pulse-forming network (PFN). The present invention replaces this analog-style network with two IGBT transistors Q1,Q2 in an active PFN configuration. In operation, these transistors are normally in a non-conducting state. This connects the flashlamps, LP1 and LP2, only across the simmer power supply 132. When an IGBT driver 134, however, is signaled to initiate the generation of the laser light pulse, trigger signals are sent to both transistors Q1, Q2. This connects the series connected Xenon flashlamps LP1,LP2 to ground through resistors R7 and R8 and across the high voltage power supply 130. The flashlamps then draw current from both the high voltage power supply and the series capacitor banks Cx and Cy.

The use of transistors Q1,Q2 to connect the flashlamps across the high voltage power supply 130 has a number of advantages relative to prior art passive PFN circuits. First, with a passive PFN, it is generally difficult to provide for selection of the pulse duration; passive pulse-forming networks are generally tuned only to generate a pulse of a single duration. In contrast, the trigger pulse provided to the IGBT transistors Q1,Q2 may be easily digitally controlled via the IGBT driver 134, allowing any desired pulse duration consistent with the laser's characteristics and power supply. This is illustrated by the pulse duration selector 135 that preferably enables the operator to select pulse durations of 5, 10, or 20 msec. The only limitation on the pulse is the current the transistors Q1 and Q2 can conduct before they begin to be damaged. This factor, however, does not provide a hard upper limit to the pulse duration generated by the network since two or more transistors may be connected in parallel to meet the electrical current demands.

Figure 5A:
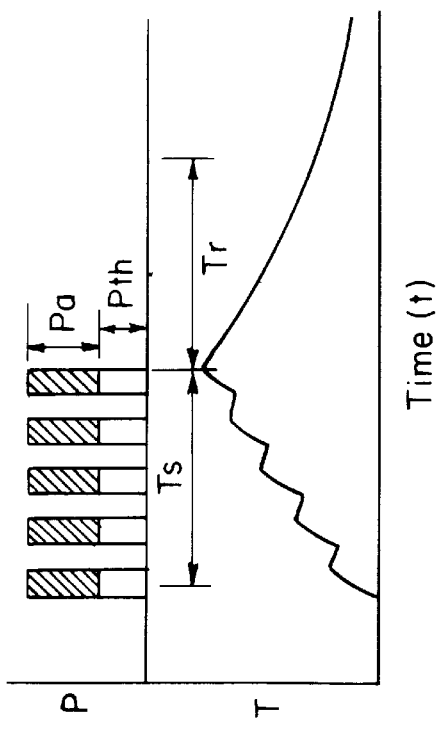
FIGS. 5A and 5B are plots of power/induced temperature as a function of time for pulse periodic heating and constant amplitude heating, respectively.

Further, the use of the active PFN additionally allows for the use of pulse periodic heating techniques. FIG. 5A is a plot of the power (P) supplied to the laser and the resulting temperature (T) of the targeted vessel as a function of time. A series of short subpulses are generated, with a fractional duty cycle over the selected effective pulse duration Ts by controlling transistors Q1 and Q2. Each subpulse has a duration of 1, 2, or 3 msec.

Figure 5B:
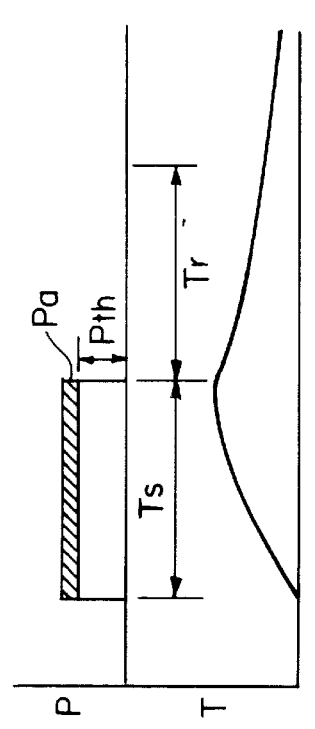

Pulse periodic heating techniques have certain advantages over constant amplitude heating shown in FIG. 5B, especially in flashlamp-excited lasers. A certain threshold of pump power Pth is needed to begin lasing in the gain media, the alexandrite. The excess flashlamp power Pa over this lasing threshold then determines the amplitude of the laser output beam. By compressing the generated light into a series of shorter pulses, a higher percentage of the pumping power used to excite the media is realized in the power of the output beam as shown by hatched regions in FIGS. 5A. In contrast, as shown in FIG. 5B, when operating the laser in a constant amplitude mode, most of the power is consumed in reaching the lasing threshold. This power is lost to heat, increasing the need for liquid cooling and the demands on the power supply.

As also shown in FIGS. 5A and 5B, the temperature rise T induced in targeted hair producing structures by the pulse periodic heating is only slightly different than that induced by the continuous amplitude heating. The tissue temperature increases in a stepwise fashion with pulse periodic heating as opposed to gradually in the continuous amplitude case. This difference in heating, however, does not affect the efficacy of the therapy because it is only the maximum temperatures that determine whether or not the structures are destroyed.

With shorter pulse durations the advantages of pulse periodic heating techniques relative to constant amplitude heat become less pronounced. Generally, in the context of the inventive system, pulse periodic heat is only required for effective pulse durations of greater than 10 msec.

Figure 6:
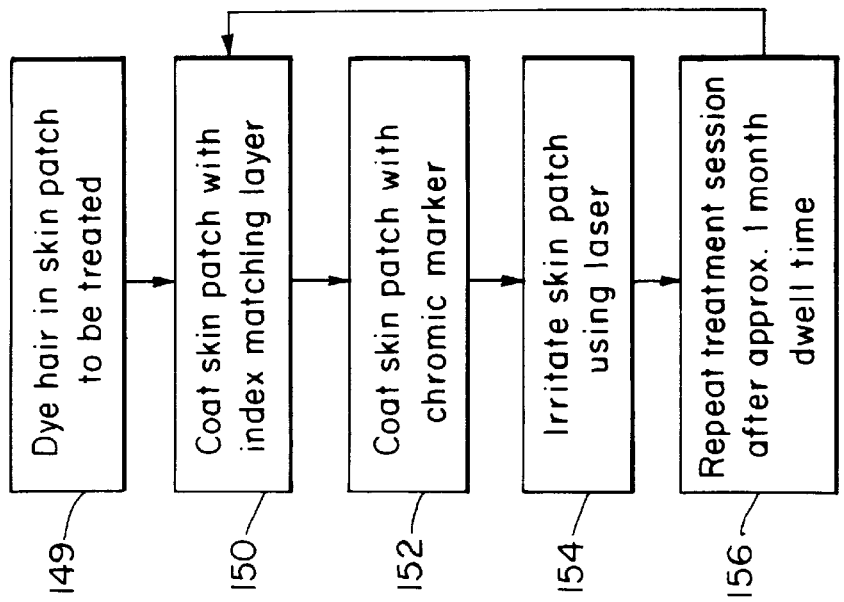
FIG. 6 is a process diagram showing hair removal according to the invention.

FIG. 6 is a method diagram showing the inventive hair removal technique using the alexandrite laser.

As a preliminary step 149, it may be helpful to have some patients first dye the hair in the skin patch to be treated. This is especially helpful for those patients having light-colored hair. The hair coloring is perform with any dark-colored commercially available hair dye. It is preferably performed by the patient in the days proceeding the laser treatment. As with these commercially hair dyes, the dyeing effect penetrates deeply into the hair shaft in the follicle to the papilla. This facilitates the absorption of the laser energy into the hair producing structures in the papilla and surrounding it, which increases selectivity.

The skin patch to be treated is first coated with the index-matching layer in step 150. The thermochromic or photochromic marker is also be coated over the skin patch in step 152 possibly with the index-matching layer.

The skin patch is then irradiated with the laser light pulse in step 154. The entire surface of the skin patch is preferably irradiated with about 20 J/cm$^2$ using separate or slightly overlapping spots on the skin. The spots are located on the skin to ensure treatment of each follicle. The number of laser light pulses needed to irradiate the skin during each application depends upon the spot size, which depends on the laser's power. A higher powered laser can achieve the 20 J/cm$^2$ of energy necessary in the 5 msec pulse duration and thus can use a larger spot size. Seven millimeters spot size represents a good trade-off between laser power available under a current technology and a spot size that is large enough to efficiently treat the areas in a reasonably time. The thermochromic or photochromic marker indicates to the operator those parts of the skin that already have been treated.

Medical experiments have suggested that better results occur if the skin patch is irradiated only once in the same treatment session. Preferably, each section of the patch should receive one 5 msec laser light pulse providing a fluence of 20 J/cm$^2$.

This protocol then is repeated after approximately month long intervening dwell intervals in step 156. Generally, the first session is not entirely successful at removing all of the hair. Those follicles that do not contain a hair shaft generally are insufficiently irradiated to terminate any future hair growth. The absence of the added absorption of the hair shaft results in lower temperatures than that necessary to sufficiently damage the hair producing structures. During the first irradiation, most of the hair follicles that contain hair are destroyed. Then, across the intervening dwell interval, those follicles that previously did not have hairs grow their own hairs so that when treatment again is performed those hair follicles showing new growth are destroyed. For complete hair removal, this process generally must be repeated three or four times with the hair re-dyeing of step 149 repeated as necessary.

While this invention has been particularly shown and described with references to preferred embodiments thereof, it will be understood by those skilled in the art that various changes in form and detail may be made therein without departing from the spirit and scope of the invention as defined by the appended claims.

What is claimed is:

1. A hair removal laser system, comprising:
   a long pulse alexandrite laser which generates a laser light output pulse having a duration greater than 10 msec, having a fluence between 10 and 50 J/cm$^2$, and being comprised of a series subpulses over its duration; and
   a light delivery system which transmits the laser light output pulse to a hair-bearing skin of a patient;
   wherein the long pulse alexandrite laser comprises:
   an alexandrite gain medium;
   at least one flashlamp which is adapted to pump the alexandrite gain medium;
   a power supply which is connected to provide power to the at least one flashlamp; and
   a flashlamp driver circuit which controls the driving of the at least one flashlamp by the power supply.

2. The system described in claim 1, wherein the flashlamp driver circuit comprises at least one transistor which switches the at least one flashlamp across the power supply.

3. The system described in claim 1, wherein the flashlamp driver circuit comprises two or more transistors which are connected in parallel to switch the at least one flashlamp across the power supply.

4. The system described in claim 1, wherein the at least one transistor is an IGBT-type transistor.

5. The system described in claim 1, wherein the flashlamp driver circuit modulates a current through the at least one flashlamp to generate the series subpulses.

* * * * *